(12) United States Patent
Pruthi

(10) Patent No.: US 6,582,733 B1
(45) Date of Patent: Jun. 24, 2003

(54) COMPOSITION FOR THE TREATMENT OF HEPATITIS INCLUDING HCV

(76) Inventor: Som C. Pruthi, 25675 Meadowview Ct., Salinas, CA (US) 93908

( * ) Notice: Subject to any disclaimer, the term of this patent is extended or adjusted under 35 U.S.C. 154(b) by 0 days.

(21) Appl. No.: 10/147,257

(22) Filed: May 15, 2002

(51) Int. Cl.⁷ .......................... A61K 33/22; A61K 9/00; A61K 47/00; A01N 65/00; A23K 1/165

(52) U.S. Cl. ........................ 424/660; 424/400; 424/725; 424/439; 424/442

(58) Field of Search ................................. 424/660, 400, 424/725, 439, 442

Primary Examiner—Christopher R. Tate
Assistant Examiner—Randall Winston
(74) Attorney, Agent, or Firm—Robert M. Downey, P.A.

(57) ABSTRACT

A composition for use in treating hepatitis includes: 4%–28% Gulancha by weight; 20%–7% Sodium Biborate by weight; 5%–47% Horseradish by weight; and 3%–14% Mysore Gamboge be weight.

6 Claims, No Drawings

COMPOSITION FOR THE TREATMENT OF HEPATITIS INCLUDING HCV

BACKGROUND OF THE INVENTION

1. Field of the Invention

The present invention relates to a composition comprising all natural ingredients and, more particularly, to an all natural composition for the treatment of inflammation of the liver such as, but not limited to, Hepatitis including HCV.

2. Discussion of the Related Art

Hepatitis is an inflammation of the liver primarily caused by a virus and, less commonly, by certain medications or toxins (e.g. alcohol). The viral infection is often acquired through exposure to contaminated blood. Those most likely to contract the virus are intravenous drug users who share contaminated needles, although sexual contact with a person who has a form of Hepatitis can also spread the disease. In some instances, healthcare workers exposed to contaminated blood and persons who need repeated transfusions of blood have acquired a form of Hepatitis.

Three main types of viral Hepatitis have been identified, namely Hepatitis A, Hepatitis B and Hepatitis C. Hepatitis A is a highly infectious form of Hepatitis and is the most common form of the disease. Hepatitis A is usually transmitted by contaminated food or water. The symptoms of Hepatitis A often are similar to those of intestinal flu and a vast majority of persons with Hepatitis A recover completely.

Acute Hepatitis B is potentially a more serious form of viral liver infection. Its symptoms are much the same as those of Hepatitis A, but the symptoms are more severe and last longer. The primary initial symptoms of Hepatitis A and Hepatitis B include poor appetite, nausea, vomiting and fever. In later stages of Hepatitis, the urine may become dark and persistent or recurring jaundice develops. In approximately 20% of cases of Hepatitis cirrhosis (scarring of the liver) eventually develops. Cirrhosis as a result of Hepatitis can be diagnosed through a blood test to evaluate liver function. Eventually, a liver affected by cirrhosis becomes tender as well.

Hepatitis C is an emerging public health problem in the United States. One distinctive feature of Hepatitis C is that the virus or viruses responsible for this condition cannot easily be identified in blood tests. It is estimated that about 4 million Americans are infected with Hepatitis C. However, because this form of Hepatitis is not easily identified, most of those infected with Hepatitis C are not aware of their condition. Patients with chronic Hepatitis C are at the greatest risk for progression to cirrhosis. Globally, an estimated 170 million people are chronically infected with Hepatitis and 3–4 million are newly infected each year.

In the United States, therapy for those infected with Hepatitis includes treatment with INTERFERON and RIBAVIRIN. The cost of treatment is considerably high and is effective with less than 50% of infected patients. Currently, no vaccine is available to prevent Hepatitis C and treatment for chronic Hepatitis is too costly for most patients.

The composition of the present invention provides an economical and natural treatment for Hepatitis, including the Hepatitis C virus.

SUMMARY OF THE INVENTION

The present invention is directed to a composition for the treatment of Hepatitis without toxicity. The composition includes all natural ingredients and has been shown to decrease the serum bilirubin to acceptable levels after 10–21 days of treatment with the composition. Specifically, the composition comprises a combination of natural ingredients including Horseradish, Gulancha, Sodium Biborate, and Mysore Gamboge. In a preferred embodiment, the composition is manufactured in the form of a powder for use in capsules, tablets, syrup or in a liquid form for subcutaneous injection.

DETAILED DESCRIPTION OF THE PREFERRED EMBODIMENTS

The composition of the present invention includes the combination of roots of Gulancha, Sodium Biborate powder, Mysore Gamboge tree gum resin and dried roots of Horseradish. According to the composition of the present invention, Horseradish is present in an amount of between 5% and 47% by weight of the composition; Sodium Biborate is present in the amount of between 20% and 87% by weight of the composition; Mysore Gamboge is present in the amount of between 3% and 14% by weight of the composition and Gulancha is present in an amount of between 4% and 28% by weight of the composition.

The Horseradish tree, known by the botanical name MORINGA OLEIFERA, is found primarily in the Himalayas in India. The roots of the Horseradish tree are known to provide essential oils and have been used in many different medicines. The present invention uses the roots of the Horseradish tree for the beneficial effects of treating liver inflammation.

Sodium Biborate is known by the botanical name Sodii Biboras. Crude Sodium Biborate occurs as a natural deposit in masses by evaporation on the shores of lakes in India and Tibet. Sodium Biborate is purified by dissolving the natural deposits in water, straining the solution through cloth and gradually drying the cloth filters in sunlight. The filtered particulate, captured by the cloth filter, is a grayish-white color.

Mysore Gamboge, known by the botanical name Garcinia Pictoria, is a tree found in the southern and eastern parts of India. The gum resin, extracted from the Mysore Gamboge tree is often used for medicinal purposes.

Gulancha, known by the botanical name Tinospora Cordifolia Miers, is a plant which grows primarily in south India. The composition of the present invention uses the roots of the Gulancha plant.

The composition of the present invention is prepared by heating Sodium Biborate on a hot plate until the particles puff in a manner similar to popcorn. These puffed particles are then ground into a fine powder for use in the composition. Excessive grinding should be avoided, as this may result in overheating and destroying the natural medicinal properties of the ingredient. Therefore, it is best to grind the Sodium Biborate particles in series of steps, wherein smaller particles are separated from the remainder of larger particles by screening. The separated smaller particles, of a predetermined maximum size, are then further ground and separated, repeating the process in a series of steps to eventually produce a fine powder. In a preferred embodiment, the process of grinding is also accomplished with use of a mortar and pestle. In a series, sieves, each having predetermined screen openings, are used to separate the ground material throughout the particle size reduction and grinding process.

Mysore Gamboge gum resin is purified by dissolving the gum resin in water and straining through a cloth. The liquid is evaporated in direct sunlight to yield dried pieces of purified gum resin which are then broken into smaller pieces. The dried broken pieces are then ground into a fine powder in various steps, similar to that set forth above in describing the processing of Sodium Biborate, to avoid excessive heating at any time in the grinding process. Commercially available grinding techniques may also be used for mass production, but care should be taken to avoid excessive heating.

Horseradish roots are first washed to remove impurities. This is achieved by soaking the roots in a water-filled pot which is large enough so that the volume of water is at least twice of that of the herb placed therein. The pot is agitated for 2–3 minutes to wash the herb at a water temperature of between 65–85 degrees Fahrenheit. Thereafter, the water is drained and the pot, containing the herb, is refilled with freshwater. This process is repeated 4–5 times until the Horseradish roots are thoroughly cleaned. The washed roots are then dried in direct sunlight and ground into a fine powder in the separation and grinding steps as set forth above in connection with Sodium Biborate.

Gulancha roots are first washed to remove impurities by soaking the roots in a water-filled pot containing a volume of water which is at least twice that of the herb placed therein. Similar to the washing process for the Horseradish roots described above, the pot is agitated for 2–3 minutes to wash the Gulancha roots, using a water temperature of between 65–85 degrees Fahrenheit. After 2–3 minutes of agitation, the water is drained and refilled with fresh water, repeating the process 4–5 times until the Gulancha roots are sufficiently cleaned of impurities. The washed Gulancha roots are then dried in direct sunlight and ground into a fine powder, following the same separation and grinding steps as outlined above in connection with the processing of Sodium Biborate.

Once all four ingredients are ground to powder form, to a desired mesh particle size, the powders are then placed in a mixer chamber (e.g. bowl or container) in accordance with their predetermined percentages by weight. The four powders are then mixed at slow speeds, by stirring, until a homogenous blend is achieved. The homogenous blend is kept in a cool, dry place until used in the manufacturing of capsules, tablets, syrup or other forms, in accordance with the manufacturing techniques which are well known in the field of drugs and dietary supplements.

In capsule form, the composition is preferably present in a concentration of between 900 mg to 1,800 mg. In capsule form, this may require taking 2–4 capsules per day, depending upon the concentration of each capsule and the prescribed dosage. The optimal dosage for most patients seems to be 900 mg per day. The capsules should be taken orally with plain yogurt in the morning. In chronic cases, two capsules taken in the morning and two capsules in the evening may be required. Improvement will ordinarily be evident in fifteen days from the beginning of treatment. The treatment should be continued, with the prescribed daily dosages, for at least three weeks. During the treatment period, alcohol, meat, drugs (other than those prescribed by a physician), spices, sour juices and fried foods should be avoided.

In order to verify the efficacy of the composition of the present invention in treating Hepatitis, several test studies were performed. The results of testing on three patients are set forth below.

EXAMPLE TEST STUDY

INITIAL LABORATORY TEST READINGS

| Patient | Serum Bilirubin (SB) (mg/dl) | SGPT (units) |
|---|---|---|
| Male, Age 36 | 9.6 | 650 |
| Female, Age 32 | 5.4 | 150 |
| Male, Age 27 | 7.6 | 325 |
| Normal Range: | 0.2 to 0.8 | 5 to 35 |

Dosage: The above patients were each administered two capsules a day, totaling 900 mg, for a period of 10–15 days. Results: Laboratory testing for SB and SGPT levels for each patient, taken after fifteen days, were in the normal range.

While the instant invention as been shown and described in accordance with a preferred and practical embodiment thereof, it is recognized that departures from the instant disclosure are contemplated within the spirit and scope of the present invention which, therefore, should not be limited except as set forth in the following claims as interpreted under the doctrine of equivalents.

What is claimed is:

1. A composition for the treatment of liver inflammation comprising the following ingredients:

Gulancha, in an amount of between 4% and 28% by weight of the composition;

Sodium Biborate, in an amount of between 20% and 87% by weight of the composition;

Horseradish, in an amount of between 5% and 47% by weight of the composition; and Mysore Gamboge, in an amount of between 3% and 14% by weight of the compositon.

2. A composition for treatment of liver inflammation comprising the following ingredients:

powder of Gulancha derived from roots of the Gulancha plant, in an amount of between 4% and 28% by weight of the composition;

powder of Sodium Biborate, in an amount of between 20% and 87% by weight of the composition;

powder of Horseradish derived from roots of the Horseradish tree, in an amount of between 5% and 47% by weight of the composition; and powder of Mysore Gamboge, derived from gum resin extracted from the Mysore Gamboge tree in an amount of between 3% and 14% by weight of the composition.

3. The composition as recited in claim 2 wherein said composition is contained in a capsule form comprising between 900 mg and 1,800 mg of said composition.

4. The composition as recited in claim 2 wherein said composition is contained in a tablet form comprising between 900 mg and 1,800 mg of said composition.

5. The composition as recited in claim 2 wherein said composition is contained in a syrup form for oral consumption in an amount of between 900 mg and 1,800 mg of said composition.

6. The composition as recited in claim 2 wherein said composition is contained in a liquid form for subcutaneous injection, wherein the composition is administered in dosages of between 900 mg and 1,800 mg.

* * * * *